(12) United States Patent
Horie

(10) Patent No.: US 7,095,498 B2
(45) Date of Patent: Aug. 22, 2006

(54) SPECTROSCOPIC ELLIPSOMETER

(75) Inventor: Masahiro Horie, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 165 days.

(21) Appl. No.: 10/791,780

(22) Filed: Mar. 4, 2004

(65) Prior Publication Data

US 2004/0233437 A1 Nov. 25, 2004

(30) Foreign Application Priority Data

May 20, 2003 (JP) ............................ P2003-141796
Nov. 26, 2003 (JP) ............................ P2003-395259

(51) Int. Cl.
*G01J 4/00* (2006.01)
(52) U.S. Cl. ..................................... 356/364
(58) Field of Classification Search ................ 356/364, 356/432, 601, 369, 563; 374/45, 5, 7
See application file for complete search history.

(56) References Cited

U.S. PATENT DOCUMENTS 4,210,401 A 7/1980 Batten
5,910,842 A 6/1999 Piwonka-Corle et al.
6,704,101 B1 * 3/2004 Rangarajan et al. ...... 356/237.2
6,714,301 B1 * 3/2004 Otsuki et al. ............... 356/369
6,784,991 B1 * 8/2004 Rotter et al. ................ 356/369

* cited by examiner

*Primary Examiner*—Hoa Q. Pham
*Assistant Examiner*—Isiaka O. Akanbi
(74) *Attorney, Agent, or Firm*—McDermott Will & Emery LLP

(57) ABSTRACT

In a spectroscopic ellipsometer (1), a lighting part (3) comprises a light source part for measurement (measurement light source) (31) and a polarizer (32), and the polarizer (32) obtains polarized light from light outputted from the measurement light source (31) and guides the polarized light to a substrate (9). A light receiving part (4) comprises an analyzer (41) on which reflected light which is the polarized light reflected on the substrate 9 is incident and a spectroscope (42), and the reflected light through the analyzer (41) enters the spectroscope (42), where a polarization state at each wavelength is acquired. The spectroscopic ellipsometer (1) has a construction in which mirrors are disposed only between the measurement light source (31) and the polarizer (32) and between the analyzer (41) and the spectroscope (42). In the spectroscopic ellipsometer (1), with this construction, the polarization state of the polarized light or its reflected light is not changed by mirrors and it is therefore possible to achieve measurements with high accuracy.

9 Claims, 3 Drawing Sheets

SPECTROSCOPIC ELLIPSOMETER

BACKGROUND OF THE INVENTION

1. Field of the Invention

The present invention relates to a spectroscopic ellipsometer which emits polarized light onto an object to acquire a polarization state of the light reflected on the object.

2. Description of the Background Art

Conventionally, a spectroscopic ellipsometer is installed in a manufacture field for semiconductor devices and used to measure thickness of a film formed on a semiconductor substrate (hereinafter, referred to as "substrate"), optical constants and the like. The spectroscopic ellipsometer emits polarized light onto a substrate to acquire a polarization state at each wavelength of the light reflected on the substrate and performs ellipsometry for some measurements on a single layer film or a multilayer film.

As such a spectroscopic ellipsometer, U.S. Pat. No. 5,910,842 discloses an apparatus which uses only reflection mirrors to guide polarized light from a polarizer to a substrate and guide the light reflected on the substrate to an analyzer, to thereby acquire a polarization state of the reflected light while suppressing occurrence of color aberration.

Recently, since miniaturization and sophistication of circuit pattern on a semiconductor device requires high precision in thickness of a film formed on a substrate, the spectroscopic ellipsometer is required to perform measurements with high accuracy. On the other hand, the spectroscopic ellipsometer is also required to reduce its size for space saving in the manufacture field.

In the method disclosed in U.S. Pat. No. 5,910,842, however, there is a possibility of changing the polarization state of light due to reflectin by the mirrors provided on an optical path between the polarizer and the analyzer or varying the polarization state of light due to some effect of thermal distortion or the like, and therefore it is difficult to acquire change of the polarization state between the light emitted to the substrate and the light reflected thereon (i.e., the polarization state of reflected light) with high accuracy. Though it is possible to suppress the change in polarization state by reducing the incident angle of light to the mirrors, this causes upsizing of the spectroscopic ellipsometer under constraints of construction.

SUMMARY OF THE INVENTION

The present invention is intended for a spectroscopic ellipsometer. A first object of the present invention is to acquire information for ellipsometry with high accuracy and a second object is to ensure size reduction of the spectroscopic ellipsometer.

According to an aspect of the present invention, the spectroscopic ellipsometer comprises a lighting part for guiding polarized light to an object, and a light receiving part for receiving reflected light which is the polarized light reflected on the object to acquire a polarization state at each wavelength of the reflected light, and in the spectroscopic ellipsometer, the lighting part comprises a light source part, and a polarizer which is a polarizing element for acquiring the polarized light from light outputted from the light source part, and at least one reflection mirror is disposed only between the light source part and the polarizer on an optical path from the light source part to the object.

The above spectroscopic ellipsometer can irradiate the object with the polarized light from the polarizer in an unchanged polarization state, to thereby increase measurement accuracy.

According to another aspect of the present invention, the spectroscopic ellipsometer comprises a lighting part for guiding polarized light to an object, and a light receiving part for receiving reflected light which is the polarized light reflected on the object to acquire a polarization state at each wavelength of the reflected light, and in the spectroscopic ellipsometer, the light receiving part comprises an analyzer which is a polarizing element on which the reflected light is incident, and a spectroscope on which the reflected light through the analyzer is incident, and at least one reflection mirror is disposed only between the analyzer and the spectroscope on an optical path from the object to the spectroscope.

The above spectroscopic ellipsometer can guide the reflected light from the object to the analyzer without changing the polarization state, to thereby increase measurement accuracy.

According to still another aspect of the present invention, the spectroscopic ellipsometer comprises a lighting part for guiding polarized light to an object, and a light receiving part for receiving reflected light which is the polarized light reflected on the object to acquire a polarization state at each wavelength of the reflected light, and in the spectroscopic ellipsometer, the lighting part comprises a light source part, a polarizer which is a polarizing element for acquiring the polarized light from light outputted from the light source part, and a plurality of rotationally-symmetric ellipsoidal mirrors disposed on an optical path from the light source part to the object through the polarizer.

Through bending (or turnaround) of the optical path by using a plurality of rotationally-symmetric ellipsoidal mirrors, it is possible to ensure size reduction of the spectroscopic ellipsometer.

According to yet another aspect of the present invention, the spectroscopic ellipsometer comprises a lighting part for guiding polarized light to an object, and a light receiving part for receiving reflected light which is the polarized light reflected on the object to acquire a polarization state at each wavelength of the reflected light, and in the spectroscopic ellipsometer, the lighting part comprises a light source part, a polarizer which is a polarizing element for acquiring the polarized light from light outputted from the light source part, another light source part for emitting auxiliary light, an optical element for superimposing the auxiliary light on light from the light source part, and a light shielding pattern disposed at a position almost optically conjugate to an aperture stop position of an optical system from the light source part to the object on an optical path from the another light source part to the polarizer, the light receiving part comprises an analyzer which is a polarizing element on which the reflected light is incident, a spectroscope on which the reflected light through the analyzer is incident, another optical element for extracting the auxiliary light from the reflected light, and an image pickup part disposed at a position optically conjugate to the light shielding pattern, for receiving the auxiliary light from the another optical element to acquire an image of the light shielding pattern, and the lighting part or the light receiving part comprises a rotation mechanism for rotating the polarizer or the analyzer.

Preferably, the spectroscopic ellipsometer further comprises an operation part for obtaining a tilt angle of a substrate from an image acquired by the image pickup part and performing ellipsometry on a film formed on the substrate on the basis of the tilt angle and the polarization state.

This makes it possible to obtain the tilt angle of the object and ensure size reduction of the spectroscopic ellipsometer.

Preferably, the optical element is a pinhole mirror disposed at a position optically conjugate to an irradiation position on the substrate, having an aperture to which light from the light source part is led while converging, and the auxiliary light is reflected on the pinhole mirror to be superimposed on the light from the light source part. Further, a pattern for focusing is formed on a reflection surface of the pinhole mirror, and the spectroscopic ellipsometer further comprises a half mirror for reflecting part of the reflected light extracted by the another optical element, another image pickup part disposed at a position optically conjugate to the pinhole mirror, for receiving light from the half mirror to acquire an image of the pattern for focusing on the substrate, and an up-and-down moving mechanism for performing focusing by vertically moving the substrate on the basis of a contrast of image acquired by the another image pickup part.

This makes it possible to ensure size reduction of the spectroscopic ellipsometer and perform focusing.

In any one of the above aspects of the present invention, preferably, the polarizer is a sheet-like polarizing element. This makes it possible to suppress some effect of color aberration in ellipsometry. Further preferably, the polarizer is a transmission-type grating polarizing element in which a plurality of metal wires are arranged on a transparent plate at constant intervals. This makes it possible to obtain the polarized light belonging to a wide range of wavelength band with stability.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
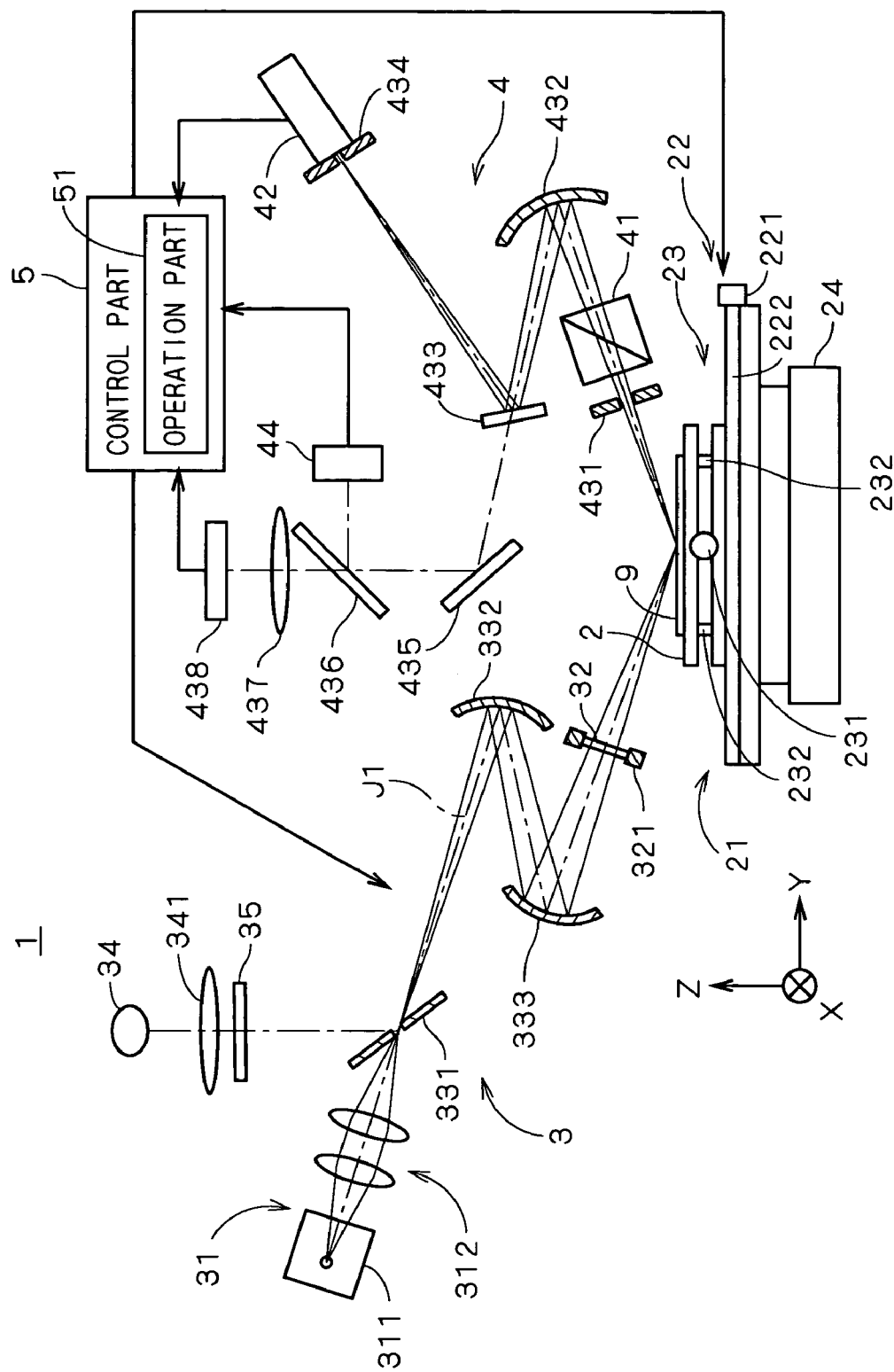
FIG. 1 is a view showing a construction of a spectroscopic ellipsometer.

FIG. 1 is a view showing a construction of a spectroscopic ellipsometer 1 in accordance with a preferred embodiment of the present invention. The spectroscopic ellipsometer 1 comprises a stage 2 on which a substrate 9 with a thin film (single layer film or multilayer film) formed thereon is mounted, a stage moving mechanism 21 for moving the stage 2 in the X direction and the Y direction of FIG. 1, a lighting part 3 for guiding polarized light onto the substrate 9, a light receiving part 4 for receiving reflected light which is the polarized light reflected on the substrate 9 and a control part 5 constituted of a CPU for performing various computations, a memory for storing various pieces of information and the like.

The lighting part 3 has a high-intensity light source part 31 for measurement (hereinafter, referred to as a "measurement light source") which emits light for ellipsometry. Polarized light is obtained from light outputted from the measurement light source 31 through a polarizer 32 which is a rotating polarizing element and the substrate 9 is irradiated with the polrized light. The light receiving part 4 has an analyzer 41 which is a polarizing element on which the reflected light from the substrate 9 is incident and the reflected light through the analyzer 41 enters a spectroscope 42, where a polarization state at each wavelength is acquired.

The stage moving mechanism 21 has a Y-direction moving mechanism 22 for moving the stage 2 in the Y direction of FIG. 1 and an X-direction moving mechanism 23 for moving the stage 2 in the X direction. In the Y-direction moving mechanism 22, a ball screw (not shown) is connected to a motor 221 and the X-direction moving mechanism 23 travels in the Y direction of FIG. 1 along guide rails 222 with rotation of the motor 221. The X-direction moving mechanism 23 has the same construction as the Y-direction moving mechanism 22, in which the stage 2 is moved in the X direction along guide rails 232 by a ball screw (not shown) with rotation of a motor 231.

The control part 5 has an operation part 51 for performing various computations and a signal from the light receiving part 4 is inputted to the operation part 51. The lighting part 3 and the stage moving mechanism 21 are also connected to the control part 5 and the control part 5 controls these constituents while performing computations, to acquire various measurement results on the basis of the ellipsometry on the film formed on the substrate 9.

Next, the lighting part 3 and the light receiving part 4 will be described in detail. The measurement light source 31 has a light source 311 having a high-intensity xenon (Xe) lamp and a group of lenses 312, and light from the light source 311 is led while converging onto a back surface side of an aperture of a plate-like pinhole mirror 331 through the group of lenses 312. The light source 311 may be another type of lamp or the like, and as required, a filter for cutting infrared rays, a chiller unit and the like may be provided.

The pinhole mirror 331 is fixed obliquely with the normal of its reflection surface being orthogonal to the X axis and inclined 70 degrees with respect to an optical axis J1, and the light (i.e., a light beam) from the measurement light source 31 is guided to an aspherical mirror 332, gradually spreading with numerical aperture (NA) of 0.02 through an aperture part of the pinhole mirror 331 (specifically, an aperture part of square shape with sides of 150 μm, two of which are parallel to the X axis and other two of which are orthogonal thereto). In this case, luminous flux section orthogonal to the optical axis J1 of light immediately after being emitted from the pinhole mirror 331 has a rectangular shape with long sides of 150 μm parallel to the X axis and short sides of 50 μm orthogonal thereto.

The aspherical mirror 332 has a reflection surface which is part of a rotationally-symmetric ellipsoidal surface, and the light entering the aspherical mirror 332 having a concave surface is further guided to an aspherical mirror 333 also having a concave surface. The aspherical mirror 333 is also a rotationally-symmetric ellipsoidal mirror like the aspherical mirror 332, and the light reflected on the aspherical mirror 333 is incident on the polarizer 32, being collected with NA of 0.1.

The polarizer 32 is a sheet-like polarizing element (including a thin-plate one) as described later and fixed in a hollow shaft positioned inside a stepping motor 321 (in other words, the polarizer 32 is disposed in a hollow portion of the hollow-type stepping motor 321). The stepping motor 321 rotates about an axis parallel to the optical axis J1 by control of the control part 5 and the light polarized in accordance with a rotation angle of the stepping motor 321 is led out of the polarizer 32 and emitted onto the substrate 9 with an incident angle of 70 degrees.

In the lighting part 3, since the optical system from the pinhole mirror 331 to the substrate 9 is a minification optical system at a ratio of 1:5, the luminous flux section orthogonal to the optical axis J1 of the polarized light near a surface of the substrate 9 has a rectangular shape with long sides of 30 µm parallel to the X axis and short sides of 10 µm orthogonal thereto. Therefore, an irradiation region of the polarized light on the substrate 9 is a very small region of square with sides of about 30 µm×30 µm.

Figure 2:
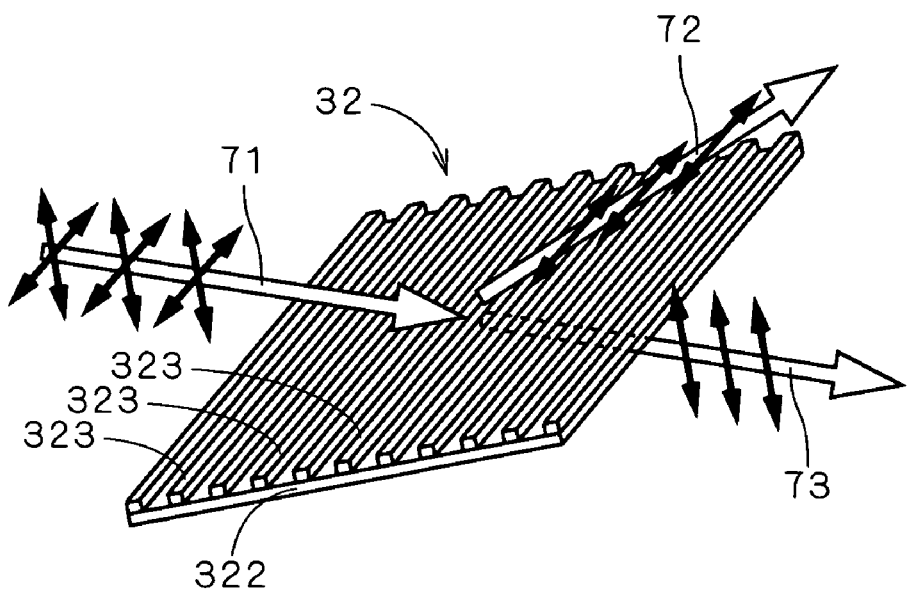
FIG. 2 is a view showing part of a polarizer.
Figure 3:
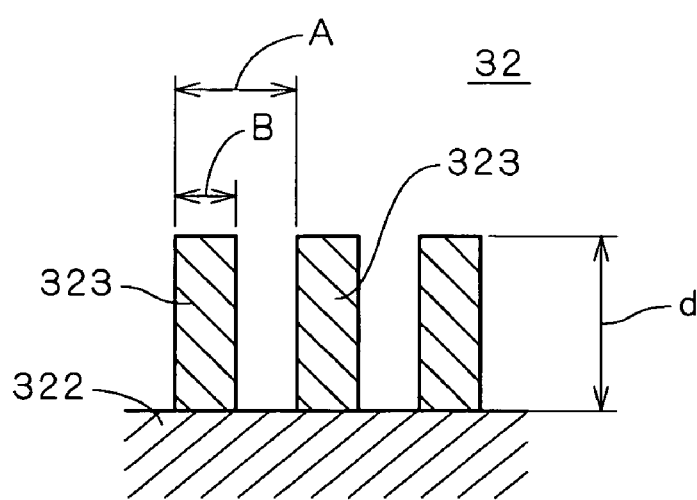
FIG. 3 is a longitudinal section showing part of the polarizer.

FIG. 2 is a view showing part of the polarizer 32 and FIG. 3 is a longitudinal section showing part of the polarizer 32. As shown in FIGS. 2 and 3, the polarizer 32 has a sheet-like transparent plate 322 formed of glass, and a plurality of metal wires 323 are formed on the transparent plate 322 by vapor deposition of e.g., tantalum (Ta). A plurality of metal wires 323 are each extended on a surface of the rectangular transparent plate 322 in a direction along one side thereof (hereinafter, referred to as a "specific direction") and arranged at regular intervals in a direction orthogonal to the specific direction as shown in FIG. 2, and thus the polarizer 32 is a transmission-type grating polarizing element called a wire grid polarizer (or a grating polarizer).

When light enters the polarizer 32 of FIG. 2 from a direction indicated by an arrow 71, a polarized component parallel to the specific direction is reflected on the metal wires 323 in a direction indicated by an arrow 72, and a polarized component orthogonal to the specific direction passes through the polarizer 32 as indicated by an arrow 73 and polarized light in accordance with the rotation angle of the rotating polarizer 32 is actually led out. Part of the polarized component of the incident light parallel to the specific direction is absorbed into the metal wires 323, generating the Joule heat by moving electrons in the metal wires 323 towards the specific direction with its electric field. In contrast to this, although the polarized component orthogonal to the specific direction also moves the electrons in the metal wires 323 with its electric field towards the direction orthogonal to the specific direction, the ratio of part absorbed into the metal wires 323 is less than that of the polarized component parallel to the specific direction due to limitation of traveling distance of the electrons.

Figure 4:
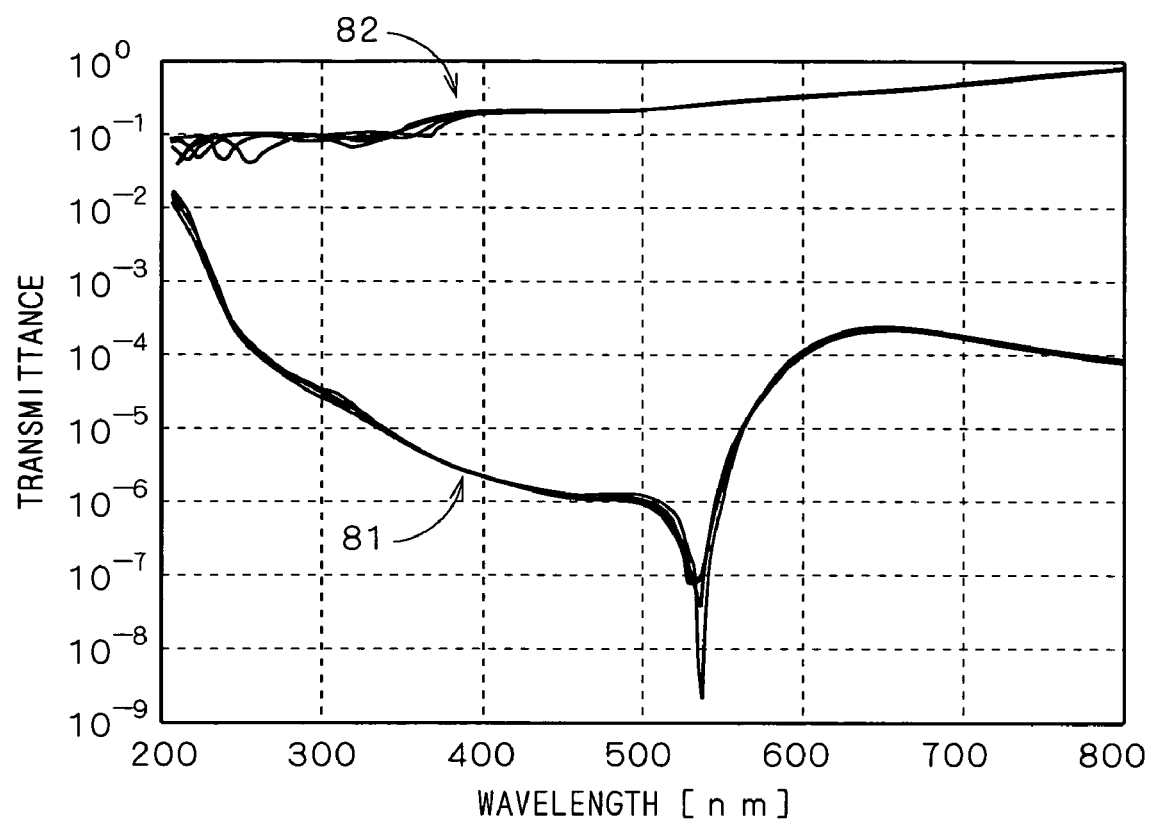
FIG. 4 is a graph showing polarization characteristics of the polarizer.

FIG. 4 is a graph showing polarization characteristics of the polarizer 32, where the height d of a metal wire 323 of FIG. 3 is 300 nm, the width B is 100 nm and the pitch A of metal wires 323 is 200 nm. The vertical axis of FIG. 4 indicates transmittance and the horizontal axis indicates wavelength. A group of lines 81 of FIG. 4 indicate spectral transmittances of polarized components parallel to the specific direction in cases where the incident angle of light to the polarizer 32 is 0, 2.5, 5, 10 and 15 degrees. A group of lines 82 similarly indicate spectral transmittances of polarized components orthogonal to the specific direction in cases where the incident angle of light to the polarizer 32 is 0, 2.5, 5, 10 and 15 degrees.

As shown in FIG. 4, the polarizer 32 has characteristic that the transmittance of the polarized component orthogonal to the specific direction indicated by the lines 82 is sufficiently larger than the transmittance of the polarized component parallel to the specific direction indicated by the lines 81 in a wide range of frequency band from 200 nm to 800 nm. It can be also seen from FIG. 4 that even if the incident angle of light to the polarizer 32 is inclined up to 15 degrees, the polarized light can be led out with stability. In other words, it can be seen that a wire grid polarizer can be used as a polarizing element for spectroscopic ellipsometer even if light is incident in a slightly oblique way. The polarizer 32 is not limited to one having such polarization characteristics as shown in FIG. 4 and the metal wire 323 may be formed of a metal other than tantalum.

As discussed above, in the lighting part 3, by the two aspherical mirrors 332 and 333 disposed only on an optical path between the measurement light source 31 and the polarizer 32, the light is guided to the polarizer 32, being collected with larger numerical aperture as compared with the light through the pinhole mirror 331, and the polarized light from the polarizer 32 is emitted to the very small region on the substrate 9 with relatively high light quantity. In that case, since a wire grid polarizer is used as the polarizer 32, which has a thin sheet-like shape and thermal stability, it is possible to obtain polarized light belonging to a wide range of wavelength band from ultraviolet to infrared while suppressing color aberration caused by the polarizer 32 within tolerance.

As shown in FIG. 1, the reflected light from the substrate 9 is drawn into a slit plate 431 and led out to the analyzer 41. An aperture part of the slit plate 431 has a rectangular shape with sufficiently long sides parallel to the X axis and short sides orthogonal thereto and its numerical aperture with respect to a direction orthogonal to the X axis (a direction which almost corresponds to height) is 0.05. This limits a range of reflection angle on the substrate 9 of the reflected light drawn into the slit board 431. On the other hand, since most of the reflected light is not limited in the X direction, a sufficient amount of light for measurement is let to the analyzer 41.

As the analyzer 41, a Rochon prism which polarizes light with high accuracy and stability is used (a sheet-like polarizing element (specifically, a wire grid polarizer) may be used like polarizer 32), and the light passing through the analyzer 41 is reflected on a spherical mirror 432 and then on a cold mirror 433, going through an aperture part of a slit plate 434, and incident on the spectroscope 42. The spectroscope 42 is preferably a Czerny-Turner spectroscope having a back-illuminated one-dimensional CCD which is cooled by a Peltier device or the like, and disperses incident light with high resolution of wavelength to measure the intensity of light with high sensitivity at each wavelength (e.g., each wavelength from ultraviolet ray to near-infrared ray). Then, the intensity of reflected light at each wavelength is associated with the rotation angle of the polarizer 32, to acquire a polarization state of the reflected light at each wavelength, specifically, a phase difference between a p-polarized component and an s-polarized component at each wavelength and an angle whose tangent gives an amplitude ratio of these reflected polarized components (i.e., a complex amplitude ratio).

The optical system from the substrate 9 to the spectroscope 42 is an optical system at a ratio of 1:1 and an aperture part of the slit plate 434 has a section of square with sides of 200 µm. Therefore, the spectroscope 42 can receive light from a rectangular region of 200 µm×600 µm on the substrate 9 which is sufficiently larger than the irradiation region of the polarized light, and even if color aberration is caused by the analyzer 41, it has little effect on the polarization state of the reflected light received by the spectroscope 42.

The lighting part 3 is further provided with an auxiliary light source part 34 having a light emitting diode for emitting additional light (an infrared light beam is used in the preferred embodiment and hereinafter it is referred to as "auxiliary light"), and auxiliary light from the auxiliary light source part 34 is guided to a pattern plate 35 through a condenser lens 341. On the pattern plate 35 formed is a predetermined light shielding pattern (e.g., cross-line scale) and the auxiliary light is guided to the pinhole mirror 331, with portions corresponding to the light shielding pattern shielded. The auxiliary light source part 34 does not necessarily have a light emitting diode only if it can generate light having wavelength different from that of the light for measurement, and the auxiliary light may be generated by a lamp.

On a reflection surface of the pinhole mirror 331 formed is a focusing pattern to be used for focusing as discussed later (e.g., grid-line scale formed away from its aperture part), and the emitted auxiliary light is reflected towards the aspherical mirror 332, being superimposed on the light from the measurement light source 31, and further guided through the aspherical mirror 333 and the polarizer 32 to the same irradiation region on the substrate 9 as for the polarized light.

At this time, since the position of the pinhole mirror 331 and the irradiation position on the substrate 9 are optically conjugate to each other (in other words, the position of the pinhole mirror 331 corresponds to a field stop position of the optical system from the measurement light source 31 to the substrate 9), an image of focusing pattern is formed outside the irradiation region of polarized light on the substrate 9. In contrast to this, since the pattern plate 35 is disposed at a position almost optically conjugate to an aperture stop position of the optical system from the measurement light source 31 to the substrate 9, no effect of light shielding pattern appears in the irradiation region of auxiliary light on the substrate 9.

The reflected light from the substrate 9 is guided to the cold mirror 433 through the slit plate 431, the analyzer 41 and the spherical mirror 432, and only auxiliary light (i.e., an infrared light beam) out of the reflected light passes through the cold mirror 433 and extracted. The auxiliary light passing through the cold mirror 433 is reflected on a mirror 435 and guided to a half mirror 436. Part of the auxiliary light is reflected on the half mirror 436 and received by a light shielding pattern pickup part (an image pickup part for light shielding pattern) 44. Since the position of the light shielding pattern pickup part 44 is optically conjugate to the position of the pattern plate 35 in the optical system from the pattern plate 35 through a surface of the substrate 9 to the light shielding pattern pickup part 44, an image of the light shielding pattern is formed on the light shielding pattern pickup part 44. Image data (or image signal) of the light shielding pattern is outputted from the light shielding pattern pickup part 44 to the control part 5.

Part of the auxiliary light which passes through the half mirror 436 is guided through a lens 437 to a substrate image pickup part 438 and received therein. Since the position of the substrate image pickup part 438 is optically conjugate to the positions of the pinhole mirror 331 and the surface of the substrate 9, the substrate image pickup part 438 acquires an image of the focusing pattern on the substrate 9. In the spectroscopic ellipsometer 1, on the basis of the contrast of an image of the acquired pattern on the substrate 9, the control part 5 vertically moves the stage up-and-down moving mechanism 24 provided under the stage 2 to control the surface level of the substrate 9 at a certain height (in other words, to perform focusing).

In measurement by the spectroscopic ellipsometer 1, an tilt angle of the substrate 9 with respect to a horizontal plane (XY plane of FIG. 1) is measured while the polarization state of the reflected light is acquired by the light receiving part 4. Specifically, emission of light is started from the measurement light source 31 and the auxiliary light source part 34, and then the spectroscope 42 acquires the polarization state of reflected one of the polarized light at each wavelength while the light shielding pattern pickup part 44 acquires an image of the light shielding pattern.

At this time, since the surface level of the substrate 9 at the irradiation position of the auxiliary light is kept constant and the position of the light shielding pattern pickup part 44 is optically conjugate to the position of the pattern plate 35 through the surface of the substrate 9 as discussed above, a position of the light shielding pattern in the image acquired by the light shielding pattern pickup part 44 becomes the position corresponding to the tilt angle of the substrate 9 (exactly, the tilt angle at the irradiation position of the auxiliary light). Therefore, a distance (vector) between a barycentric position of the light shielding pattern in the image acquired by the operation part 51 and a barycentric position of the light shielding pattern in an image for tilt angle of 0 degree which is stored in advance is calculated and the tilt angle of the substrate 9 (e.g., a vector indicating a direction of normal of the substrate 9) is thereby obtained.

After the tilt angle of the substrate 9 and the polarization state of the reflected light are acquired, the operation part 51 performs ellipsometry on the film on the substrate 9 by using an accurate incident angle which is obtained from the tilt angle (and direction of tilt), on the basis of the acquired polarization state, to acquire measurement results such as optical constants and thickness of the film.

As discussed above, in the spectroscopic ellipsometer 1 of FIG. 1, on the optical path from the measurement light source 31 to the spectroscope 42 through the surface of the substrate 9, the reflection mirrors are not provided between the polarizer 32 and the analyzer 41 but provided only between the measurement light source 31 and the polarizer 32 and between the analyzer 41 and the spectroscope 42. This makes it possible to emit the polarized light from the polarizer 32 onto the surface of the substrate 9 in an unchanged polarization state and guide the reflected one of the polarized light to the analyzer 41 without changing the polarization state. As a result, the spectroscopic ellipsometer 1 can acquire the change in polarization state of the polarized light through reflection and the polarization state of reflected one of the polarized light with high accuracy and stability, to achieve ellipsometry on a film formed on the substrate 9 with higher accuracy.

Since a plurality of reflection mirrors (especially, two aspherical mirrors 332 and 333) are arranged between the measurement light source 31 and the polarizer 32, the lighting part 3 can be made compact by bending the optical path a plurality of times. Further, since part of the optical system for measurement of the tilt angle of the substrate 9 (specifically, the optical system from the auxiliary light source part 34 to the light shielding pattern pickup part 44 through the surface of the substrate 9) and part of the optical system for acquisition of the polarization state (specifically, the optical system from the measurement light source 31 to the spectroscope 42 through the surface of the substrate 9) are common in the spectroscopic ellipsometer 1, it is possible to ensure size reduction of the spectroscopic ellipsometer 1.

Particularly, since the reflection mirrors are not provided between the polarizer 32 and the analyzer 41 but provided only between the pinhole mirror 331 and the polarizer 32 and between the analyzer 41 and the cold mirror 433 on the optical path from the pinhole mirror 331 to the cold mirror 433 through the surface of the substrate 9 in the spectroscopic ellipsometer 1, the light from the measurement light source 31 and the auxiliary light can be collectively reflected, to ensure size reduction of the spectroscopic ellipsometer 1 as well as above-discussed increase in accuracy of ellipsometry.

A plurality of reflection mirrors between the measurement light source 31 and the polarizer 32 may include other types of mirrors such as turning mirrors, as required.

Though the preferred embodiment of the present invention has been discussed above, the present invention is not limited to the above-discussed preferred embodiment, but allows various variations.

Though the stepping motor 321 is provided on the polarizer 32 in the above preferred embodiment, a stepping motor may be provided on the analyzer 41. In this case, the polarization state of the reflected light at each wavelength to be acquired by the light receiving part 4 can be acquired correspondingly to a rotation angle of the analyzer 41. The polarizer 32 and the analyzer 41 may be provided with other types of rotation mechanisms.

Though no reflection mirror is provided between the polarizer 32 and the analyzer 41 on the optical path from the measurement light source 31 to the spectroscope 42 through the surface of the substrate 9 in the above preferred embodiment, a reflection mirror may be provided either between the polarizer 32 and the substrate 9 or between the substrate 9 and the analyzer 41, depending on accuracy for measurement required in the spectroscopic ellipsometer, convenience of design and the like. Particularly, only for the purpose of size reduction of the spectroscopic ellipsometer, a plurality of (possibly three or more) rotationally-symmetric ellipsoidal mirrors may be disposed at any position on the optical path from the measurement light source 31 to the substrate 9 through the polarizer 32.

The pattern plate 35 is not necessarily disposed between the auxiliary light source part 34 and the pinhole mirror 331 but may be disposed at any position on the optical path from the auxiliary light source part 34 to the polarizer 32 only if the position of the pattern plate 35 is almost optically conjugate to the aperture stop position of the optical system from the measurement light source 31 to the substrate 9.

An optical element for superimposing the auxiliary light onto the light from the measurement light source 31 may be an element other than the pinhole mirror 331, and for example, may be a half mirror. Similarly, an optical element for extracting the auxiliary light out of the reflected light may be an element other than the cold mirror 433.

Depending on a structure of the spectroscopic ellipsometer 1 (especially, cooling structure) and a wavelength band to which the polarized light to be used for measurement belongs, for example, a sheet-like polarizing element in which silica glass is coated with a PVC (poly vinyl chloride) film or the like to form a dichroic film (in other words, a film with anisotropy of high-molecular material) may be used as the polarizer 32.

The substrate 9 is not limited to a semiconductor substrate but may be, for example, a glass substrate used in a liquid crystal display or other flat panel displays. A film formed on an element other than the substrate on which a fine pattern is formed can be measured in the spectroscopic ellipsometer 1.

While the invention has been shown and described in detail, the foregoing description is in all aspects illustrative and not restrictive. It is therefore understood that numerous modifications and variations can be devised without departing from the scope of the invention.

What is claimed is:

1. A spectroscopic ellipsometer comprising: a lighting part for guiding polarized light to an object; and a light receiving part for receiving reflected light which is said polarized light reflected on said object to acquire a polarization state at each wavelength of said reflected light, wherein said lighting part comprises: a light source part; a polarizer which is a polarizing element for acquiring said polarized light from light outputted from said light source part; another light source part for emitting auxiliary light; an optical element for superimposing said auxiliary light on light from said light source part; and a light shielding pattern disposed at a position almost optically conjugate to an aperture stop position of an optical system from said light source part to said object on an optical path from said another light source part to said polarizer, said light receiving part comprises: an analyzer which is a polarizing element on which said reflected light is incident; a spectroscope on which said reflected light through said analyzer is incident; another optical element for extracting said auxiliary light from said reflected light; and an image pickup part disposed at a position optically conjugate to said light shielding pattern, for receiving said auxiliary light from said another optical element to acquire an image of said light shielding pattern, and said lighting part or said light receiving part comprises a rotation mechanism for rotating said polarizer or said analyzer.

2. The spectroscopic ellipsometer according to claim 1, further comprising an operation part for obtaining a tilt angle of a substrate from an image acquired by said image pickup part and performing ellipsometry on a film formed on said substrate on the basis of said tilt angle and said polarization state.

3. The spectroscopic ellipsometer according to claim 1, wherein said optical element is a pinhole mirror disposed at a position optically conjugate to an irradiation position on said substrate, having an aperture to which light from said light source part is led while converging, and said auxiliary light is reflected on said pinhole mirror to be superimposed on said light from said light source part.

4. The spectroscopic ellipsometer according to claim 3, wherein a pattern for focusing is formed on a reflection surface of said pinhole mirror, said spectroscopic ellipsometer further comprising: a half mirror for reflecting part of said reflected light extracted by said another optical element; another image pickup part disposed at a position optically conjugate to said pinhole mirror, for receiving light from said half mirror to acquire an image of said pattern for focusing on said substrate; and an up-and-down moving mechanism for performing focusing by vertically moving said substrate on the basis of a contrast of image acquired by said another image pickup part.

5. The spectroscopic ellipsometer according to claim 1, wherein at least one reflection mirror is disposed only between said optical element and polarizer on an optical path from said optical element to said object.

6. The spectroscopic ellipsometer according to claim 1, wherein at least one reflection mirror is disposed only between said analyzer and said another optical element on an optical path from said object to said another optical element.

7. The spectroscopic ellipsometer according to claim 1, further comprising a plurality of rotationally-symmetric ellipsoidal mirrors disposed on an optical path from said optical element to said object through said polarizer.

8. The spectroscopic ellipsometer according to claim 1, wherein said polarizer is a sheet-like polarizing element.

9. The spectroscopic ellipsometer according to claim 8, wherein said polarizer is a transmission-type grating polarizing element in which a plurality of metal wires are arranged on a transparent plate at constant intervals.

* * * * *